United States Patent
Laurent et al.

(10) Patent No.: US 10,595,627 B1
(45) Date of Patent: Mar. 24, 2020

(54) ADAPTIVE BRUSHING CYCLE

(71) Applicant: Willo 32 SAS, Limoges (FR)

(72) Inventors: Alexandre Georges Gabriel Laurent, Brooklyn, NY (US); Hugo De Gentile, Feytiat (FR); Jil Abed Michel Chabaro, Antony (FR)

(73) Assignee: Willo 32 SAS, Limoges (FR)

( * ) Notice: Subject to any disclaimer, the term of this patent is extended or adjusted under 35 U.S.C. 154(b) by 0 days.

(21) Appl. No.: 16/270,101

(22) Filed: Feb. 7, 2019

(51) Int. Cl.
*A61C 17/34* (2006.01)
*A46B 15/00* (2006.01)
*A61C 17/02* (2006.01)
*A61C 17/22* (2006.01)

(52) U.S. Cl.
CPC ...... *A46B 15/0008* (2013.01); *A46B 15/0012* (2013.01); *A61C 17/0211* (2013.01); *A61C 17/228* (2013.01)

(58) Field of Classification Search
CPC ....... A61C 17/16; A61C 17/22; A61C 17/221; A61C 17/222; A61C 17/225; A61C 17/227; A61C 17/30; A61C 17/32; A61C 17/38; A61B 15/0012; A61B 2200/1066; A46B 15/0008
See application file for complete search history.

(56) References Cited

U.S. PATENT DOCUMENTS

| | | | | |
|---|---|---|---|---|
| 4,223,417 A * | 9/1980 | Solow | ................... | A46B 9/045 15/167.2 |
| 5,943,723 A * | 8/1999 | Hilfinger | ................ | A61C 17/22 15/105 |
| 7,082,638 B2 | 8/2006 | Koh | | |
| 7,537,451 B1 | 5/2009 | Ramnarine | | |
| 7,683,153 B2 * | 3/2010 | Schile | ................ | C08G 59/4014 525/533 |
| 8,359,692 B2 * | 1/2013 | Brewer | .................. | A46B 9/045 15/167.2 |
| 8,448,282 B2 | 5/2013 | Stapelbroek | | |
| 8,617,090 B2 | 12/2013 | Fougere | | |
| 8,635,731 B2 | 1/2014 | Garner | | |
| 8,667,634 B2 | 3/2014 | Steur | | |
| 8,677,541 B2 * | 3/2014 | Meadows | .......... | A61C 17/0211 15/22.1 |
| 8,745,802 B2 | 6/2014 | Steur | | |
| 8,789,227 B2 * | 7/2014 | Cook | ................. | A46B 15/0002 15/22.1 |
| 8,863,346 B2 | 10/2014 | Headstrom | | |
| 8,978,189 B1 | 3/2015 | Sexton | | |
| 8,990,992 B2 | 3/2015 | Stapelbroek | | |
| 9,084,655 B2 | 7/2015 | Sahoo | | |
| 9,277,980 B2 | 3/2016 | Leveling | | |

(Continued)

FOREIGN PATENT DOCUMENTS

| | | | |
|---|---|---|---|
| EP | 2654609 B1 | 3/2018 | |
| EP | 2654611 B1 | 4/2018 | |

(Continued)

*Primary Examiner* — Ralph A Lewis (74) *Attorney, Agent, or Firm* — Daylight Law, P.C.

(57) ABSTRACT

An oral care appliance for cleaning teeth of a user and a method of adapting a brushing cycle of the oral care appliance are disclosed. Specific embodiments disclosed herein adapt the at least one brushing cycle based on a variety of factors, either alone or in combination, such as the time elapsed since a last brushing event and the identity of a user.

32 Claims, 4 Drawing Sheets

(56) References Cited

U.S. PATENT DOCUMENTS

| | | | |
|---|---|---|---|
| 9,308,065 B2 | 4/2016 | Steiner | |
| 9,427,078 B2 * | 8/2016 | Farrell | A46B 7/04 |
| 9,498,053 B2 * | 11/2016 | Patel | A46B 15/0006 |
| 9,504,542 B2 * | 11/2016 | De Gentile | A61C 17/0211 |
| 9,526,597 B2 | 12/2016 | Steur | |
| 9,636,195 B2 | 5/2017 | Wolpo | |
| 9,636,197 B2 | 5/2017 | Khangura | |
| 9,668,840 B2 | 6/2017 | Miller | |
| 9,907,633 B2 * | 3/2018 | Wolpo | A61N 1/0428 |
| 10,188,203 B2 * | 1/2019 | Van Gool | A46B 15/0022 |
| 2004/0134000 A1 * | 7/2004 | Hilfinger | A46B 15/0002 |
| | | | 15/22.1 |
| 2007/0184404 A1 | 8/2007 | Johnki | |
| 2010/0024143 A1 * | 2/2010 | Dickie | A46B 5/00 |
| | | | 15/167.1 |
| 2010/0281636 A1 * | 11/2010 | Ortins | A46B 9/04 |
| | | | 15/4 |
| 2011/0275424 A1 * | 11/2011 | Schmid | A46B 15/0002 |
| | | | 463/1 |
| 2016/0113745 A1 | 4/2016 | Golub | |
| 2016/0135581 A1 | 5/2016 | Pai | |
| 2016/0206415 A1 | 7/2016 | Kraft | |
| 2016/0270892 A1 | 9/2016 | Yoo | |
| 2017/0367801 A1 | 12/2017 | Fitzgerald | |
| 2018/0000573 A1 | 1/2018 | Miller | |
| 2018/0184795 A1 | 7/2018 | Pai | |
| 2018/0184857 A1 | 7/2018 | Pai | |

FOREIGN PATENT DOCUMENTS

| | | |
|---|---|---|
| WO | 2017061980 A1 | 4/2017 |
| WO | 2017146366 A1 | 8/2017 |
| WO | 2018160986 A1 | 9/2018 |

* cited by examiner

ADAPTIVE BRUSHING CYCLE

BACKGROUND OF THE INVENTION

Dental cleaning plays a significant role in impacting the overall health of an individual. Many people schedule frequent visits to a dentist for regular checkups and cleaning operations. Many oral care appliances have been developed over the years to achieve the purpose of oral hygiene to provide cleaning results by eradicating the food remains, plaque, etc. from the spaces in between the teeth. Although such appliances require less user intervention in their operations and some of these are also suitable for people with disabilities or reduced mobility or people on the move for whom it is difficult to use a traditional toothbrush, it is necessary to provide and improve existing oral care appliances for ensuring satisfactory cleaning results.

In order for such oral care appliances and practices to be effective, a high degree of user compliance is required, which many users, particularly children and the elderly, find difficult to apply. For example, user may under-do or overdo the brushing either by not following the recommended brushing process or time spent per tooth or vigorously apply non-uniform pressure while brushing. Both forms of non-compliance can result in the degradation of a person's dental health.

Therefore, a need has arisen for an oral care appliance that is configured to address one or more of the above-mentioned disadvantages and improve the dental health of a user by improving the effectiveness and user satisfaction of such oral care appliances and systems.

SUMMARY OF THE INVENTION

Specific embodiments of the present invention disclosed herein relate generally to an oral care appliance for cleaning teeth and a method of adapting a brushing cycle of the oral care appliance. The oral care appliance can comprise an adapting means configured to adapt the at least one brushing cycle based on a time elapsed since a last brushing event performed by the user. The oral care appliance may be used for cleaning, whitening and in other general oral care applications.

In specific embodiments of the invention, the oral care appliance comprises a mouthpiece configured to be actuated during at least one brushing cycle, a means to supply a cleaning agent into the mouthpiece during the at least one brushing cycle, and an adapting means configured to adapt the at least one brushing cycle based on a time elapsed since a last brushing event performed by the user.

The brushing cycle can be operated according to a plurality of operational characteristics. These operational characteristics can vary depending on operation, the type of mouthpiece utilized, or other components of the oral care appliance. The operational characteristics can be defined by at least one of the user, an operator, a health care professional, at least one default cycle, or a combination thereof. As used herein, the term "operator" refers to a person trained to operate the dental care appliance for another person. For example, a representative of the company that manufactured and/or marketed the dental care appliance who has been tasked with assisting customers with use of the dental care appliance. The operational characteristics may or may not have a defined value prior to the modification.

In specific embodiments of the invention, the adapting means can be configured to adapt the brushing cycle by modifying at least one of the operational characteristics. The adapting means can be configured to adapt the brushing cycle according to a personalized program.

In specific embodiments of the invention, the at least one default cycle can be based on at least one of a time-controlled mode, a volume-controlled mode, a pressure-controlled mode, a frequency-controlled mode, a user-specific mode, or a combination thereof.

In specific embodiments of the invention, the brushing cycle can comprise at least one contraction phase of the mouthpiece and at least one relaxation phase of the mouthpiece.

In specific embodiments of the invention, the plurality of operational characteristics, as modified by the adapting means, can comprise a defined duration, a defined count, a defined pressure, a defined amount, a defined performance indicator, a type of mouthpiece and a type of cleaning agent. The defined duration can be based on at least one of a duration of the brushing cycle, a duration of the contraction phase, a duration of the relaxation phase, a duration between the contraction phase and the relaxation phase, or a combination thereof. The defined count can be based on at least one of a count of the contraction phases, a count of the relaxation phases, a count of injections of the cleaning agent, or a combination thereof. The defined pressure can be based on at least one of a contraction pressure threshold of the contraction phase, a relaxation pressure threshold of the relaxation phase, or a combination thereof. The defined amount is based on at least one of an amount of the cleaning agent being supplied into the mouthpiece, a composition of the cleaning agent being supplied into the mouthpiece, or a combination thereof.

In specific embodiments of the invention, a cleaning agent can be supplied to a mouthpiece of the oral care appliance during a brushing cycle. The cleaning agent can be selected from one or more of a liquid, solid, powder, gel, fluid, or a combination thereof. The means to supply the cleaning agent comprises a connection assembly and at least one supply tank. The mouthpiece can comprise a flexible membrane configured to deform in response to pressure variations caused in a cavity. The pressure changes can result in volume changes of the cavity. The volume of the cavity can decrease in the contraction phase. The volume of the cavity can increase in the relaxation phase. The cavity can be formed between the mouthpiece and the dental arch of a user.

In specific embodiments of the invention, the adapting means comprises at least one of a microprocessor, a microcontroller, a memory module, a communication module, a user interface module, a display module, a timer, a counter, a monitoring means, a clock, a user identification module, or a combination thereof. The monitoring means may further comprise one or more sensors configured to monitor values of one or more of the following, but not limited to, one or more performance indicators of the oral care appliance, pressure, amount/volume, temperature, pH value, flow etc. In a specific example, the pressure in the cavity or the pressure difference between the components of the oral care appliance is monitored. In another specific example, amount/volume of the cleaning agent being injected into the mouthpiece is monitored. Therefore, the adapting means can be configured to monitor one or more operational characteristics of the brushing cycle.

In specific embodiments of the invention, the adapting means is configured to identify the user. The user can be identified by using a user interface module, a user identification module, or a communication module (e.g., an NFC chip or any other means such as Bluetooth or Wi-Fi connection of the user's smartphone). The user interface module can include a user interface on the oral care appliance itself. In a specific example, the communication module of the adapting means is used to identify the user. The functions of the user identification module may be performed by software or a combination of the software and hardware of the oral care appliance. In another specific example, a smartphone application can be used to give a command to the oral care appliance by communicating with the adapting means and adapt the brushing cycle accordingly.

In specific embodiments of the invention, the adapting means is configured to measure the time elapsed since a last brushing event performed by the user.

In specific embodiments of the invention, the adapting means is configured to store at least a brushing profile of the user in the memory module. The brushing profile can comprise at least one of the time elapsed since a last brushing event performed by the user, a specific information of the user, a record of previous brushing events performed by the user, or a combination thereof. The brushing profile of the user comprises information corresponding to one or more of the following parameters: the user's physical characteristics, the user's medical/dental record, the user's saliva analysis results, a log of pressure readings inside the user's mouth and a profile of the user, or a combination thereof. In a specific example, the oral care appliance may launch a softer cycle and adapt the brushing cycle accordingly if the user is a child. In another specific example, the pressure inside the user's mouth is recorded so as to adapt the brushing cycle if the pressure does not reach the threshold value due to the mouth shape of the user or any other physical characteristic(s) of the user.

In specific embodiments of the invention, the adapting means is configured to communicate with an online source. The default cycle can be chosen from an online database by user/operator/health care professional via the oral care appliance itself or the smartphone application. Optionally, one or more operational characteristics corresponding to the default cycle(s) can be defined/customized by the user/operator/health care professional.

In specific embodiments of the invention, the user has no access to the default cycle(s) and the changes/modification in the default cycles or operational characteristics of the default cycle(s) to adapt the brushing cycle can only be done by the health care professional.

Specific embodiments of the invention include a method of adapting at least one brushing cycle of an oral care appliance. The method comprises: identifying a user by determining an identify. The method also comprises determining a time elapsed since a last brushing event performed by the user. The method also comprises adapting the at least one brushing cycle based on the time elapsed since a last brushing event performed by the user.

In specific embodiments of the invention the dental appliance is configured to precisely control the amount/composition of cleaning agent, for example dentifrice or water, thereby causing adequate cleaning of his/her teeth. Similarly, the user-to-user variation in other parameters such as duration/number of injections of the cleaning agent, type of the cleaning agent, type of mouthpiece, duration/number of contraction/relaxation phases, contraction/relaxation pressure threshold, any performance indicator(s), any other operational characteristic(s) of the brushing cycle or the technique to supply the cleaning agent can be realized to adapt the brushing cycle. This user-to-user variation can be realized automatically or defined by at least one of the user, an operator, a health care professional, at least one default cycle, or a combination thereof.

In specific embodiments of the invention the at least one brushing cycle is adapted according to the preferences or clinical requirements or any other information of a specific user. Further, the oral care appliance is configured to identify a particular user and adapt the brushing cycle automatically. Furthermore, the brushing cycle can be adapted based on a personalized program or a list of default or customized cycles.

In specific embodiments of the invention one or more operational characteristics of the brushing cycle can be modified freely or within a certain range based on the time elapsed since a last brushing event performed by the user. This modification can be done automatically or by a user/operator/health care professional. In a specific example, the health care professional can advise the user or set the operational characteristic(s) himself to ensure a personalized usage or a personalized program. The personalized program can be goal driven meaning that the user/operator/health care professional can aim for an oral care objective over a chosen period of time such as getting the user's teeth whiter in one month, curing a periodontitis over three weeks, preparing the user for a surgical operation happening in two months, etc. According to another specific example, a disinfecting cleaning agent can be used, with longer cycles and stronger contractions of the mouthpiece to ensure proper oral hygiene before the surgical operation. Many modifications are possible to adapt the at least one brushing cycle which is operated according to the plurality of operational characteristics.

In specific embodiments of the present invention, adaptation of the brushing cycle is based on the time elapsed since a last brushing event performed by a user. Further, adaptation of the brushing cycle can be done by modifying at least one operational characteristic of the brushing cycle. For example, operational characteristic(s) such as, but not limited to, amount/composition of cleaning agent, duration/number of injections of the cleaning agent, type of cleaning agent, type of mouthpiece, duration/number of contraction/relaxation phases, contraction/relaxation pressure threshold, any performance indicator(s), etc. can be modified to adapt the brushing cycle. These principles can be applied to any oral care appliance(s) for cleaning teeth where the operational characteristic(s) of the brushing cycle can vary based on the specific type of oral care appliance or other component(s) of the oral care appliance utilized in the brushing cycle. In particular, these principles can be applied to any oral care appliance including a mouthpiece configured to be actuated during at least one brushing cycle where the operational characteristics regard the interaction of the mouthpiece with the user's teeth.

DETAILED DESCRIPTION

Aspects of the present invention can be understood by reference to the figures and description set forth herein. However, the following descriptions, and numerous specific details thereof, are given by way of illustration and not of limitation. Many changes and modifications to the specific descriptions may be made without departing from the spirit and scope thereof, and the present invention includes all such modifications. It is to be understood that the disclosed embodiments may or may not overlap with each other. Thus, part of one embodiment, or specific embodiments thereof, may or may not fall within the ambit of another, or specific embodiments thereof, and vice versa.

Figure 1:
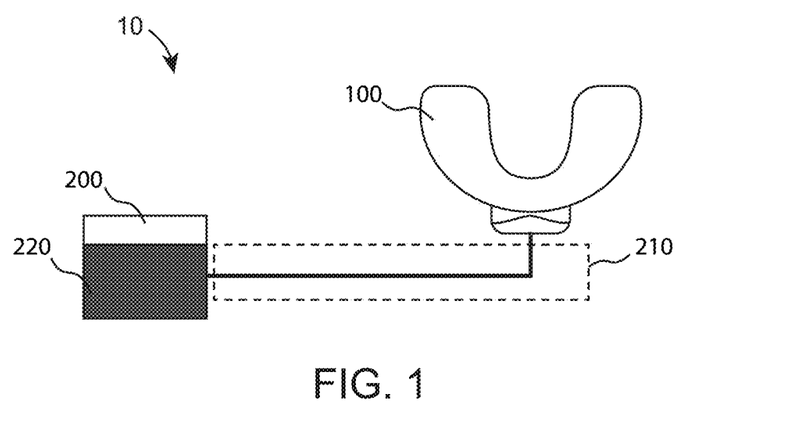
FIG. 1 illustrates an oral care appliance 10 in accordance with specific embodiments of the present invention.

FIG. 1 shows an oral care appliance 10 for cleaning teeth of a user according to a specific embodiment of the invention. The oral care appliance 10 comprises a mouthpiece 100 configured to be actuated during at least one brushing cycle and means to supply a cleaning agent into the mouthpiece 100 during the at least one brushing cycle, wherein the means to supply the cleaning agent comprises a connection assembly 210 and at least one supply tank 200 to store a cleaning agent 220. The oral care appliance 10 further comprises an adapting means configured to adapt the at least one brushing cycle based on a time elapsed since a last brushing event performed by the user. The cleaning agent referred to herein could be: a polishing agent such as an inert abrasive; a cleaning agent such as fluoride, activated charcoal, or a fluoride-fee antibacterial composition; a halitosis treatment agent such as chlorine dioxide; or a whitening agent such as hydrogen peroxide. The cleaning agent could also be any mixture of these kinds of agents and chemicals.

The connection assembly 210 can further comprise at least one pipe or conduit and at least one valve. At least one propelling means can also be operatively engaged to the connection assembly 210 or to the mouthpiece 100 directly to generate a flow of the cleaning agent 220 into the mouthpiece 100 by push or pull operation. According to specific embodiments of the present invention, a positive pressure can also be applied in the at least one supply tank 200 to facilitate the supply of the cleaning agent 220 into the connection assembly 210 or the mouthpiece 100. Positive pressure in the at least one supply tank 200 leads to a positive pressure difference between the supply tank 200 and the connection assembly 210 or the mouthpiece 100, thus causing a fluid movement from the supply tank 200 to the connection assembly 210 or the mouthpiece 100. Alternatively, the cleaning agent 220 can be dispensed via a dispenser device or a tube.

Figures 2A, 2B:
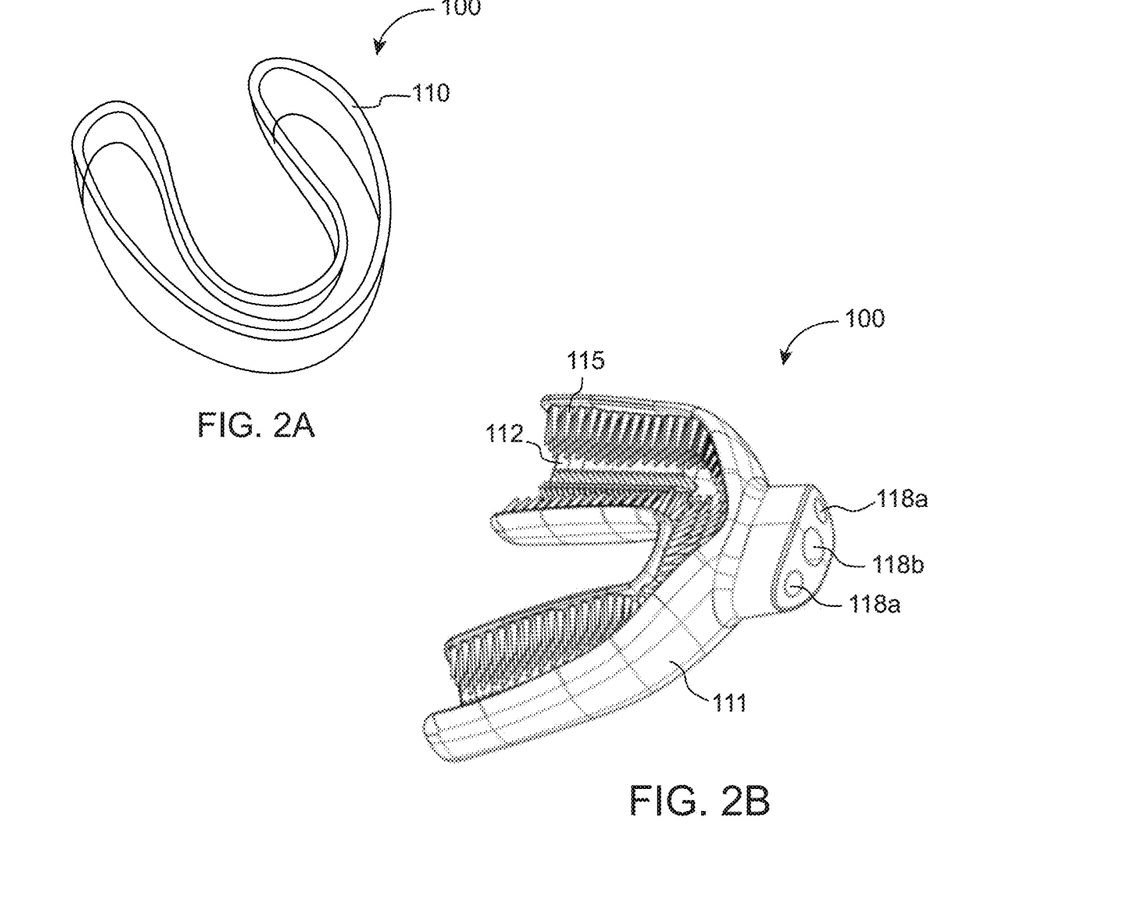
FIG. 2A illustrates a perspective view of a mouthpiece 100 in accordance with specific embodiments of the present invention.
FIG. 2B illustrates a perspective view of the mouthpiece 100 in accordance with specific embodiments of the present invention.

According to specific embodiments of the invention, the mouthpiece 100, as illustrated in FIG. 2A, comprises a flexible membrane 110 configured to deform in response to pressure variations caused in a cavity resulting in volume changes of the cavity and cleaning/oral care action in the user's mouth. The volume of the cavity can increase or decrease depending on the pressure variations in the cavity. A positive pressure in the cavity increases its volume and a negative pressure in the cavity decreases its volume.

According to specific embodiments of the invention, the mouthpiece 100 as illustrated in FIG. 2B, comprises an outer membrane 111 and an inner membrane 112. The outer membrane 111 and the inner membrane 112 can be made up of similar or different materials compatible to be used in oral care. In a particular embodiment the outer membrane 111 is made of rigid material to drive the deformation of the inner membrane 112 toward the teeth. In another embodiment, the shape of the outer membrane 111 is designed to favor the amplitude and gripping pressure of the deformation of the inner membrane 112 toward particular areas of the dentition to improve their cleaning. This particular feature can be achieved by having discontinuity of the volume of the cavity or cavities, the thickness, the material, rigidity or the shape of the outer membrane 111 or any other of its characteristics.

The mouthpiece 100 further comprises of a plurality of holes 118a, 118b for injecting/draining of a fluid/cleaning agent/oral care solution into/from the mouthpiece 100. In particular examples, the at least one-hole 118a can be used for injecting the fluid inside the mouthpiece 100 and the at least one-hole 118b for draining the fluid/waste out of the mouthpiece 100. In some further particular examples, the plurality of holes 118 can be placed on any position in the mouthpiece 100. In a different example, a single hole 118 can be used for injecting/draining the fluid/cleaning agent/oral care solution. In another example of the invention, the injection hole 118a is placed in close proximity to the draining hole 118b. During operation of the oral care cycle, injection of liquid through the at least one hole 118a can be in excess and thus can prove uncomfortable for the user. The short distance between the at least one hole 118a and the draining hole 118b can allow the excess of such a liquid to be immediately drained out of the of the mouthpiece.

According to a specific example, fluid/waste is drained out and ambient air is injected into the mouthpiece 100 to relax the mouthpiece 100. This process can be repeated multiple times in the at least one brushing cycle until all the waste is drained out or can be repeated a fixed number of times. In another example, the mouthpiece 100 comprises numerous injection and aspiration ports on its inner membrane 112 to distribute both the aspiration and the injection of fluid evenly in the mouthpiece 100 and thus on the gums and dentition of the user.

According to another embodiment of the invention, a plurality of bristles 115, attached to the inner membrane 112, are used to remove plaque, debris, inter-dental particles, tartar, biofilm etc. inside the mouth. The bristles 115 may be of shape, but not limited to, conical, cylindrical, flat, pointed tip, tapered, star-shaped, Zig-Zag which may be glued, over molded or attached to the inner membrane 112 by other different means. The outer membrane 111 is configured for contacting the gum of the user, providing comfort and good hermeticity to the cavity formed by the mouthpiece 100.

According to specific embodiments of the invention, the mouthpiece 100 is preferably in the form of a denture or a U-shape, C-shape, horseshoe shape, or any other shape configured for easy insertion inside the mouth of the user, thereby providing good comfort and good placement on the dental arch of the user. The mouthpiece 100 is preferably made up of flexible/soft material suitable for medical use or oral care. This allows easy insertion inside the mouth of the user providing comfort and reversible deformation. The mouthpiece 100 according to specific embodiments of the invention can be made up of flexible material impermeable to gases (such as air), liquids (water, cleaning liquid, disinfecting liquid) and any solid (waste particles, debris); such as latex or silicone compatible with a medical or oral care use. Thermoplastic elastomer (TPE) are suitable as flexible materials for oral care applications. They are copolymers consisting in a physical mix of polymers having plastic and elastomeric properties. Furthermore, they have a suitable temperature range of operation, between −10° C. and 80° C. They can have good food and medical grade properties as well as an absence of significant creep. Furthermore, they have good tearing and tensile strength. This makes TPEs suitable for constituting the flexible material of the mouthpiece 100.

Silicone is another polymer suitable as flexible material for oral care applications. It is a very stable polymer with low chemical reactivity. Furthermore it is stable over a large range of temperature (between −100° C. and 250° C.). It also has excellent creep, tear strength and elongation properties. In addition, it also has good food and medical grade properties making suitable for the flexible material of the mouthpiece 100.

For pleasing of the eyes, the inner and outer surface of the mouthpiece can be colored or transparent with visual effect or not, textured or not.

In specific embodiments of the invention, the mouthpiece 100 is configured to provide the cleaning action with the mechanical force applied by the cleaning elements/bristles 115 on the teeth. The mechanical action in the cleaning elements/bristles 115 can be generated by pressure variations in the cavity. The pressure variations inside the cavity makes it inflate or deflate, thus moving the cleaning elements 115 towards or away from the teeth. Moreover, the pressure variations in the cavity with respect to ambient pressure, result in the brushing cycle comprising at least one contraction phase and at least one relaxation phase of the mouthpiece 100. Further, the mechanical action in the cleaning elements/bristles 115 happens during the contraction/relaxation phase. The mechanical action of the cleaning elements 115 can consist of rubbing, sliding, deforming, rotating, vibrating or any other particular movement on the surface of the teeth of the user, or any combination thereof.

In specific embodiments of the invention, the cavity is a closed or nearly closed space formed between the mouthpiece 100 and the dental arch of the user when the mouthpiece 100 is placed on the dental arch.

In specific embodiments of the invention, the mouthpiece 100 can be an inflatable mouthpiece configured to deform in response to pressure variations in at least one cavity of the inflatable mouthpiece itself. The at least one cavity in case of the inflatable mouthpiece is formed inside the mouthpiece 100 between the inner membrane 112 and the outer membrane 111. The pressure decreases relative to ambient pressure in the at least one cavity of the mouthpiece 100, wherein the mouthpiece 100 is inflatable, may result in relaxation phase of the mouthpiece 100 and vice-versa.

In specific embodiments of the invention, the oral care appliance 10 may be configured to facilitate customized/personalized dental care by providing the user with the option of choosing a particular type of mouthpiece 100 from a plurality of different available options, for example, but not limited to, a conventional toothbrush, an electric toothbrush, a rinse, a flosser or a jet spray or other similar dental cleaning devices.

In specific embodiments of the invention, the mouthpiece 100 can be customized/personalized for use by a specific user, in that the mouthpiece 100 has been formed based on a dental imprint, 3D scan, X-ray scan, anatomic characteristics measured by a health care professional, or combination thereof of the particular user and is thus substantially complementary in shape to the corresponding dental arch of the user. Such customization of the shape of the mouthpiece 100 promotes satisfactory dental cleaning to the user and ensures a comfortable fit of the mouthpiece 100 in the user's mouth as well as oral care operation when the user uses the oral care appliance 10.

In specific embodiments of the invention, the arrangement and configuration of the plurality of bristles 115 can be customized for a specific user based on one or more focus areas corresponding to an identified dental problem area of the corresponding specific user. Examples of such arrangements and configurations include, but not limited to, width, height, shape, stiffness, material and spacing of the bristles 115.

In specific embodiments of the invention, the cleaning action on teeth of the user by the oral care appliance 10 may be carried out in at least one brushing cycle. Each of the brushing cycles comprises a sequence of at least one contraction phase of the mouthpiece 100 and at least one relaxation phase of the mouthpiece 100. In a specific example, each of the contraction phase and the relaxation phase of the mouthpiece 100 are achieved due to pressure variations caused in the cavity. During the contraction phase, a negative pressure relative to ambient pressure in the cavity decreases the volume of the cavity. While during the relaxation phase, a positive pressure relative to ambient pressure in the cavity increases the volume of the cavity. In specific embodiments of the invention an adapting means can operate in combination with at least one pump, vacuuming unit, valve mechanism, or any other actuator in the oral care appliance 10 to help to create pressure variations during its operation and/or supply the cleaning agent 220 into the mouthpiece 100 during the brushing cycle. A pump transforms electrical energy in mechanical work used to move fluid from or into cavity of the mouthpiece 100. This fluid movement increases or decreases the pressure inside the cavity of the mouthpiece 100. The pump can be a one-way pump (e.g., a hermetic pump that does not let fluid or air pass when turned off), a two-way pump, a vacuum pump, a tailor-made pump, a hermetic pump generally, or a peristaltic pump. The valve mechanism can comprise one or more solenoid valves, servo-valves, pneumatic control valves, electronic valves with pinch valves, membrane valves, or a combination thereof. As will be described in more detail below, the adapting means can work in combination with these components in order to adapt the operational characteristics of the brushing cycle.

In specific embodiments of the invention, each brushing cycle may further comprise at least one injection cycle for injecting the cleaning agent 220 into the mouthpiece 100. In a specific example, the cleaning agent 220 can be supplied into the mouthpiece 100 by injecting more than one time during a brushing cycle. In other words, each brushing cycle may comprise more than one injection or injection cycle of the cleaning agent 220. In another specific example, the cleaning agent 220 can be supplied into the mouthpiece 100 during some or one of the brushing cycles. In other words, each brushing cycle may not necessarily comprise injection of the cleaning agent 220.

In specific embodiments of the invention, the brushing cycle may be operated in the form of vibration patterns of the mouthpiece 100 to ensure proper cleaning of teeth of the user. The brushing cycle may be adapted to operate at customizable vibration frequency range. In some examples, the vibration frequencies may include, but not be limited to, sonic frequency range or ultrasonic frequency range. The sonic frequency range is the range of frequencies between 20 Hz and 20 kHz. The ultrasonic frequency range is the range of frequencies between 20 kHz and 20 MHz. Therefore, the nature and type of operational characteristics may vary depending on the operating principle of the oral care appliance 10 in general and the mouthpiece 100 in particular.

In specific embodiments of the invention, the brushing cycle may be operated according to a plurality of operational characteristics, wherein the plurality of operational characteristics comprises a defined duration, a defined count, a defined pressure, a defined amount, a defined performance indicator, a type of mouthpiece and a type of cleaning agent.

In specific embodiments of the invention, the defined duration is based on duration of the brushing cycle, duration of the contraction phase, duration of the relaxation phase, duration between the contraction phase and the relaxation phase, or a combination thereof.

In specific embodiments of the invention, the defined count is based on a count of the contraction phases, a count of the relaxation phases, a count of injections of the cleaning agent, a count of contraction phases in the brushing cycle, a count of relaxation phases in the brushing cycle, or a combination thereof.

Figure 3:
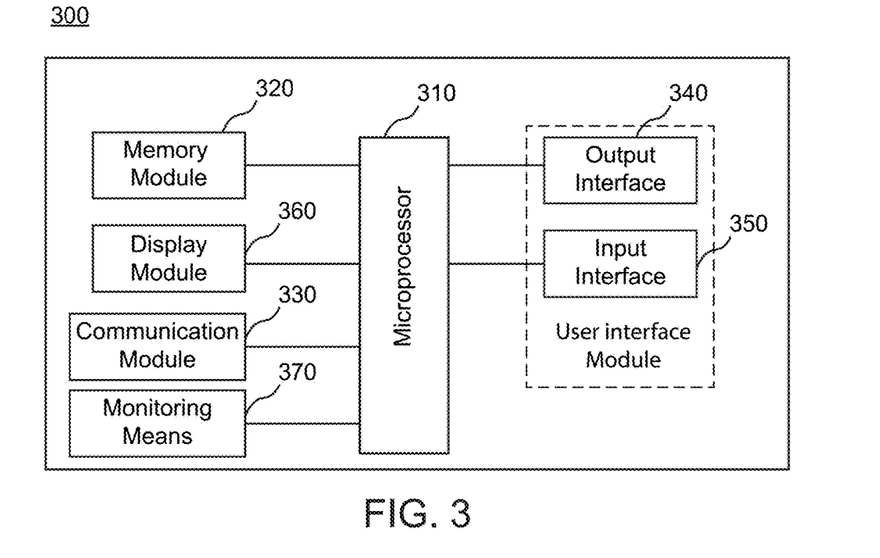
FIG. 3 illustrates an adapting means 300 in accordance with specific embodiments of the present invention.

In specific embodiments of the invention, the defined pressure is based on a contraction pressure threshold of the contraction phase, a relaxation pressure threshold of the relaxation phase, or a combination thereof. In a specific example, a contraction pressure threshold can be defined as a certain pressure level to reach in the cavity during the contraction phase of the mouthpiece 100 and a relaxation pressure threshold can be defined as a certain pressure level to reach in the cavity during relaxation phase of the mouthpiece 100. Further, the pressure can be monitored via a monitoring means 370 (as shown in FIG. 3) of the adapting means 300. The monitoring means 370 comprises at least one sensor and provides live measurements of the pressure in the cavity. The monitoring means providing live measurements of the pressure in the cavity can be an absolute or differential pressure gauge, a diaphragm gauge, a force balance sensor, a strain gauge or any other mean designed to measure the pressure of the fluid entering the mouthpiece 100 known to a person skilled in the art. The adapting means 300 uses this information to adapt the at least one brushing cycle by controlling the pump(s)/valve(s) in the oral care appliance 10.

In specific embodiments of the invention, the defined amount is based on an amount of the cleaning agent being supplied into a mouthpiece, a composition of a cleaning agent being supplied into a mouthpiece, or a combination thereof.

In specific embodiments of the invention, the defined performance indicator is based on the age, wear and/or tear of the oral care appliance 10 or any other component such as, but not limited to, the mouthpiece 100, the supply tank 200 or the like which may be utilized to determine the need for the replacement of the components.

In specific embodiments of the invention, the defined performance indicator is based on recognition of errors such as bad hermeticity, leaks, bad placement of the mouthpiece 100 in the mouth of the user, bad movement of the cleaning elements 115 on the teeth of the user, bad injection of the cleaning agent, clogged tubes or connections, absence of the supply tank 200 or any other indicator that may affect the performance of the oral care appliance 10.

In specific embodiments of the invention, the adapting means 300 is configured to manage and store (in memory module 320 or in any other database) a plurality of the operational characteristics. The plurality of the operational characteristics can be defined as per a brushing profile of the user. The brushing profile of the user corresponds to a specific user associated with the oral care appliance 10 (i.e. a user of a mouthpiece 100). Moreover, the oral care appliance is configured to identify multiple users and operate according to their respective brushing profiles. The operational characteristics, and the brushing profile of the user, can be stored in association with an identity of the user in memory module 320 or in any other database. The database can include a mapping between such identities and operational characteristics.

In specific embodiments of the invention, the brushing profile of the user includes, but is not limited to, the time elapsed since a last brushing event performed by the user, specific information of the user, a record of previous brushing events performed by the user, or a combination thereof. The specific information of the user can comprise information corresponding to one or more of the following parameters: the user's physical characteristics, the user's medical/dental record, the user's saliva analysis results, a log of pressure readings inside the user's mouth and a profile of the user, or a combination thereof. User preferences can also be stored as a part of the brushing profile. The specific information of the user can include any idiosyncratic clinical information associated with the user.

In specific embodiments of the invention, the at least one brushing cycle is adapted according to the preferences or clinical requirements or any other information of a specific user such as user's age, sex, user's physical characteristics, enamel health, gum sensitivity, periodontal condition, personalized programs, missing tooth, mouth geometry, presence or absence and type of dentures, oral sphere environment etc. Furthermore, the adapting means 300 of the oral care appliance 10 can be configured to identify a particular user and adapt the brushing cycle automatically. The oral care appliance can include stored instructions to execute this process and can determine the identity of the user using the processes disclosed below.

In specific embodiments of the invention, the oral care appliance 10 is configured to operate the brushing cycle(s) according to the one or more operational characteristics mentioned above (e.g., duration, count, pressure, amount) defined by the user, an operator, a health care professional, one or more default cycles, or a combination thereof.

According to specific embodiments of the invention, the adapting means 300 of the oral care appliance 10 is configured to adapt the at least one brushing cycle based on a time elapsed since a last brushing event performed by the user. In other words, the adapting means 300 is configured to identify and track the timeline of user's brushing regime in real-time. As such, if the user has skipped some brushing timeline, the adapting means is configured to adapt the brushing cycle by modifying one or more operational characteristics of the brushing cycle during the next brushing regime. In a specific example, the brushing cycle is adapted considering the brushing regime or brushing history of the user such as, but not limited to, brushing time, brushing frequency, brushing pattern, recommended brushing location, usage of cleaning agent/fluid, last brushing event, or a combination thereof.

In specific embodiments of the invention, the oral care appliance 10 may be pre-programmed to automatically perform the at least one brushing cycle in a predefined sequence in accordance with the at least one default cycle based on one or more control modes, wherein the control modes comprise a time-controlled mode, a volume-controlled mode, a pressure-controlled mode, a frequency-controlled mode, a user-specific mode, a biomarker detection mode, or a combination thereof. In a specific example, the control mode for the oral care appliance 10 is the time-controlled mode in which a preset time is used to control the at least one contraction phase and at least one relaxation phase of the mouthpiece 100. In another specific example, the control mode for the oral care appliance 10 is the volume-controlled mode in which a preset volume is used to control volume of the cleaning agent 220 injected into the mouthpiece 100 or fluid/waste extracted from the mouthpiece 100. In other words, the brushing cycle is controlled based on a volume of fluid that flows through the device. In another specific example, the control mode for the oral care appliance 10 is the pressure-controlled mode in which a preset pressure value is used to control pressure in the cavity. The pressure-controlled mode can be achieved by using the means for varying pressure and the monitoring means 370, thereby controlling the at least one contraction phase and at least one relaxation phase of the mouthpiece 100. In another specific example, the control mode for the oral care appliance 10 is the smart depression mode, where a combination of preset pressure value and preset time is used for controlling at least one contraction phase and at least one relaxation phase. In other words, the smart depression mode will prevent the user from waiting for an indefinite time if it takes time to reach a preset pressure value in the cavity due to leaks or any other performance indicator(s). In another specific example, the control mode for the oral care appliance 10 is the frequency-controlled mode in which a preset number of brushing cycles or contraction/relaxation phases over a particular period of time is used to control pressure in the cavity. In another specific example, the control mode for the oral care appliance 10 is the user-specific mode which is based on pre-recorded default cycles, such as, but not limited to, sensitive cycle, classic cycle, day cycle, night cycle, long cycle, short cycle, child cycle, elder cycle, softer cycle, non-exhaustive cycle, or the like. In yet another specific example the control mode for the oral care appliance 10 is the biomarker detection mode, wherein a pre-set amount of biomarker is monitored by bio-sensors of the monitoring means 370 to control the at least one contraction phase and at least one relaxation phase of the mouthpiece 100. In a specific example, if the blood level in the saliva is too high the brushing cycle is adapted in order to prevent pain of the user. In another example, if the glucose level measured in the saliva of the user reaches a specific threshold the brushing cycle is adapted to favor a deep cleaning of the oral environment of the user.

In specific embodiments of the invention, the adapting means 300 can be configured to receive a prescription from a health care professional in real-time, thereby resulting in adaptation of the at least one brushing cycle for the user by modifying one or more operational characteristics in accordance with the prescription. The prescription may be based on dental characteristics and/or preferences of the user, for example, but not limited to, the contours or shape of the dental arch of the user, the user's diet, the chemistry of the user's mouth, the user's medical/dental record, etc. The prescription can be received through the use of communication module 330 via a network connection to which the health care professional has access.

In specific embodiments of the invention, the adapting means 300 is configured to adapt the brushing cycle according to a personalized program put in place to reach one or more definite goals. The personalized program set by or for the user may include, but not limited to, whiter teeth in one month, curing periodontitis over three weeks, preparing the user for a surgical operation happening in two months or the like. Moreover, the goals or personalized programs may be adjusted over time as appropriate for the user, given the prevailing circumstances. The adaptation of the brushing cycle may include modifying the operational characteristics such as, but not limited to, a type of cleaning agent, a type of mouthpiece, amount/composition of cleaning agent, duration of the brushing cycle, duration between the contraction phase and the relaxation phase, duration/number of injections of the cleaning agent, duration/number of contraction/relaxation phases, contraction/relaxation pressure threshold, any performance indicator(s), any other operational characteristic(s) of the brushing cycle. According to a specific example, a disinfecting cleaning agent can be used, with longer cycles and stronger contractions of the mouthpiece to ensure a perfect oral hygiene before the surgical operation. Therefore, a number of modifications are possible to adapt the at least one brushing cycle which is operated according to the plurality of operational characteristics.

In specific embodiments of the invention, a health care professional can advise the user or set the operational characteristic(s) himself to ensure a personalized usage or a personalized program.

In specific embodiments of the invention, the adapting means 300 is configured to adapt the at least one brushing cycle based on the brushing profile of the user, wherein the brushing profile comprises information corresponding to at least the time elapsed since a last brushing event performed by the user.

The cleaning agent 220 may be selected from one or more of a liquid, solid, powder, gel, fluid, or a combination thereof. In the case of a cleaning agent 220 in the form of a powder, it is mixed with a diluting liquid thanks to a dedicated mixing system such as a venturi assembly, a mixing chamber or any other mixing mean. The mixed solution is then injected as a homogenous fluid with a pressure difference between the mouthpiece 100 and the supply tank(s) 200. In the case of a cleaning agent in the form of a gel, the cleaning agent might also be injected thanks to a pressure difference between the mouthpiece 100 and the supply tank 200. However, if the viscosity of the gel is too high this solution would take too much time. If so, the solution could be integrated inside a handle close to the mouthpiece 100 to reduce the injection duration, diluted in a diluting solution and then injected as a liquid solution or injected with a higher pressure thanks to a worm screw, a piston, a peristaltic pump or any other dedicated distributor.

The injection of the cleaning agent 220 can be repeated several times during the brushing cycle to increase the overall injected volume of the cleaning agent 220. In a specific example, the amount or volume of the cleaning agent 220 can be regulated by use of the monitoring means 370 and/or software associated with the oral care appliance 10. The monitoring means 370 may comprise of at least one sensor which can be put at any suitable place to function in the oral care appliance 10.

The oral care appliance 10 may be configured to adapt the brushing cycle by modifying the sequence of contraction/relaxation phases based on identification of the cleaning agent 220 or any other operational characteristic(s). For example, a whitening solution may be used with more contraction cycles to homogenize the cleaning agent 220, or an anti-periodontitis solution can be applied with lower pressure to avoid hurting an ill user.

The brushing cycle can be adapted by modifying the one or more operational characteristics via the adapting means. Further, the adapting means can be configured to adapt the at least one brushing cycle based on the time elapsed since a last brushing event performed by the user.

Referring to FIG. 3, the adapting means 300 can include one or more microprocessors 310 in communication with a memory module 320. The microprocessor 310 computes the commands to be sent to the pumps/valves of the oral care appliance 10. The memory module 320 include a non-transitory computer-readable medium which stores executable instructions for the method steps disclosed herein including determining an identity of the user, adapting the operational characteristics of the brushing cycle, and determining a time elapsed since the last brushing event. In a specific embodiment, the adapting means 300 generate a command for the pumps/valves of the oral care appliance 10. This command can take a lot of signal form such as linear, sinusoidal, ramps, successive plates, see-saw signal, exponential or any other signal form known to the person skilled in the art. Any other processor-based device such as an application specific processor or a microcontroller can also be used in place of microprocessor 310 to perform a similar function. The memory module 320 may be configured to store a variety of information, including any user information, dental history of the user, information related to the brushing profile of the user or any other useful information. The memory module 320 may also contain a set of executable instructions that affect operation of the microprocessor 310. The memory module 320 may be erasable/writable non-volatile memory, such as flash memory, dynamic volatile memory, or other suitable memory including replaceable memory media, or combinations thereof. The microprocessor 310 can be coupled to a display module 360, an input interface 350 and an output interface 340. The input interface 350 and the output interface 340 collectively forms a user interface module. The adapting means 300 may further comprise a communication module 330 to enable the communication with external networks, a user's smartphone, components of the oral care appliance 10, an online source, a health care service provider accessible network, etc.

As shown in FIG. 3, the adapting means 300 may also include the monitoring means 370 as disclosed above. The monitoring means 370 may further comprise sensor(s) configured to monitor values of one or more of, but not limited to, the following: performance indicator(s) of the oral care appliance, pressure, amount/volume, temperature, pH value, flow, blood presence, glucose quantity, other biomarkers quantity etc. The monitoring means 370 may also include an accelerometer, gyroscope, camera, or any combination thereof.

The sensors measuring pressure can be an absolute or differential pressure gauge, a diaphragm gauge, a force balance sensor, a strain gauge or any other mean designed to measure the pressure of a fluid known to a person skilled in the art.

The sensors measuring volume can be a scale, a float ball, a displacer, a differential pressure sensor, a microwave sensor, a conductivity probe, an optical sensor or any other mean designed to measure a volume known to a person skilled in the art.

The sensors measuring temperature can be a thermocouple, an infrared thermometer, a thermal camera, an ultrasonic temperature sensor, a negative temperature coefficient thermistor, a resistance temperature detector, a semiconductor-based temperature sensor, or any other mean designed to measure a volume known to a person skilled in the arts.

The sensors measuring pH can be a potentiometric pH sensor, a chemically based pH meter, pH indicator or any other mean designed to measure pH known to a person skilled in the arts.

The sensors measuring flow can be a Pitot tube, a differential pressure based flow meter, a volumetric based flow meter, turbine based flow meter, a velocity measurement based flow meter or any other mean designed to measure the flowrate of a fluid known to a person skilled in the art.

As shown in FIG. 3, the adapting means 300 may further include various components used to determine a time elapsed since a last brushing event such as a timer, a counter, a clock, a network connection to a time source and a memory for storing time stamps, and any other module or component for measuring a duration of time.

The adapting means 300 may further include various components to determine an identity such as a biometric fingerprint sensor, a user interface for receiving a credential, a mouthpiece identifier for indirectly identifying a user by identifying their mouthpiece, etc. In general, the adapting means 300 may include a user identification module for this purpose as described below.

In a specific embodiment of the invention, the output interface 340 includes one or more devices, such as, but not limited to, a speaker, LED(s), tactile/haptic feedback device, a vibrator, motors, etc. The input interface 350 includes one or more devices such as, but not limited to, a microphone, a touchscreen/touchpad input, a face recognition camera, and other input buttons or controls.

In a specific embodiment of the invention, the display module 360 is configured to display images, icons, texts, graphics, or video. The display module can enable a user to review a record of brushing activity or analyze other aspects of their usage of the oral care device. Display module 360 can be embedded in the adapting means 300 (as shown in FIG. 3). In some examples, the display module 360 can be embedded in a detached display mounted on any surface, such as a wall or mirror, or resting on a stand. The display module could alternatively be in a user's smartphone.

In specific embodiments of the invention, the communication module 330 is configured to communicate with other external communication entities such as a smartphone or detached display. Accordingly, the communication module 330 includes one or more wireless antennas configured to use one or more communication protocols (e.g., WiFi, Bluetooth, wireless USB etc.). Optionally, the communication module 330 may include one or more communication ports (e.g., USB ports). In some examples, the communication module 330 supports bi-directional short-range communication with a wireless range of no more than 100 cm.

Figure 4:
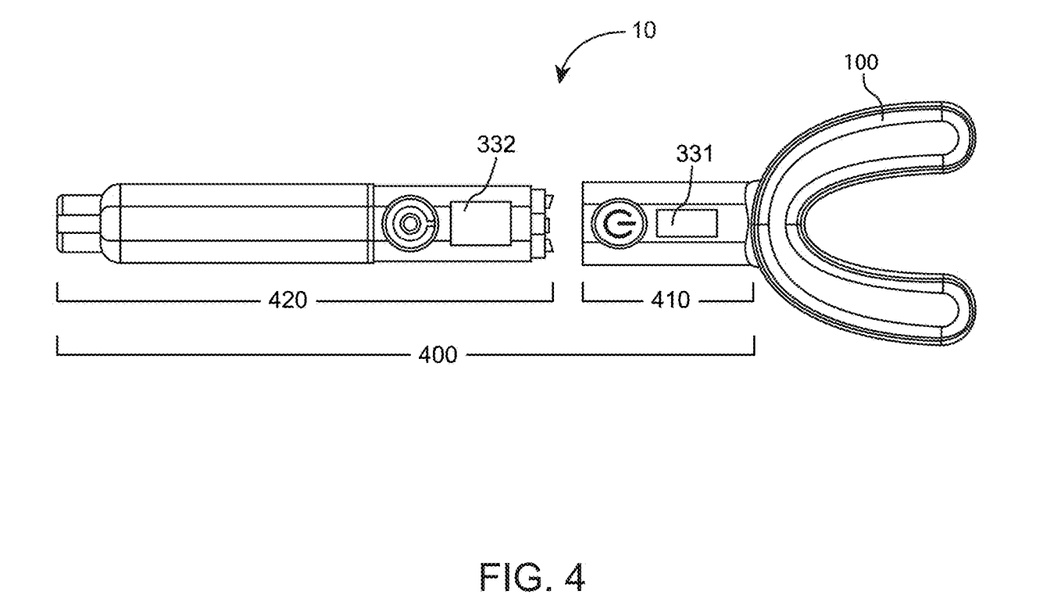
FIG. 4 shows the mouthpiece 100 connected to a handle 400 divided into at least two tubular parts (i.e., a first part 410 and a second part 420) in accordance with specific embodiments of the present invention.

In specific embodiments of the invention, the communication module 330 is specifically arranged to communicate in accordance with the Near Field Communication (NFC) standard which is designed to provide very short-range communication. An NFC module comprises an NFC tag 331 and an NFC reader 332 (as shown in FIG. 4). The NFC tag 331 comprises an electronic chip that contains encoded information and an antenna that transmits and/or receives information (including information stored in the chip). The NFC reader 332 processes (e.g. decode, de-encapsulate, etc.) the data transmitted from the NFC tag 331.

In specific embodiments of the invention, the oral care device is divided into at least two parts that can exchange information. The components can transmit the information related to the last brushing event performed by the user, for example, day, date, brushing time, brushing pattern used, elapsed time since last brushing, or the like. Additionally, the transmitted information may include identification data, and data that can be used to determine an identity of the user (i.e. user identifier), usage information, or other information defined by the brushing profile. Identification data can comprise the name, age, sex or occupation of the user, and the usage information can comprise the recommended usage time (e.g., 2 minutes per brushing cycle), usage of cleaning agent/fluid, recommended brushing pressure or location, personalized program associated with the user, predefined brushing cycles or the like. The identity of the user, as used herein, refers to an idiosyncratic system-level identifier used to associate data with a particular user across a platform of components. For example, the identity can be used to store a brushing profile of a particular user in a network accessible database and to retrieve that data when a particular oral care device in the system determines that it is being used by that particular user. As another example, the identity can be used to store and retrieve data between parts of an oral care appliance handle.

The division of labor between storing user data and identifying a user can be split between the components in various ways. For purposes of this disclosure, the portion of the device that is closer to the mouth of the user can be referred to as a proximate component while devices further from the mouth of the user can be referred to as a distal component. In specific embodiments of the invention, a proximate component, such as a mouthpiece, can include data used to identify a user which can be transmitted to a distal component, such as a handle, and used to retrieve a brushing profile for that user, or other data needed to apply the proper regime to a user. The distal component can then assure that new data collected during additional brushing cycles is stored by the system in association with that identity. In specific embodiments of the invention, a proximate component can additionally, or in the alternative, store the brushing profile, usage data, or other data directly. The data can then be delivered to a distal component and be used to actuate a set of brushing cycles in accordance with the regimen needed by that particular user. In turn, the distal component can update any usage data stored in the proximate component after the brushing cycles have been completed.

Figure 5:
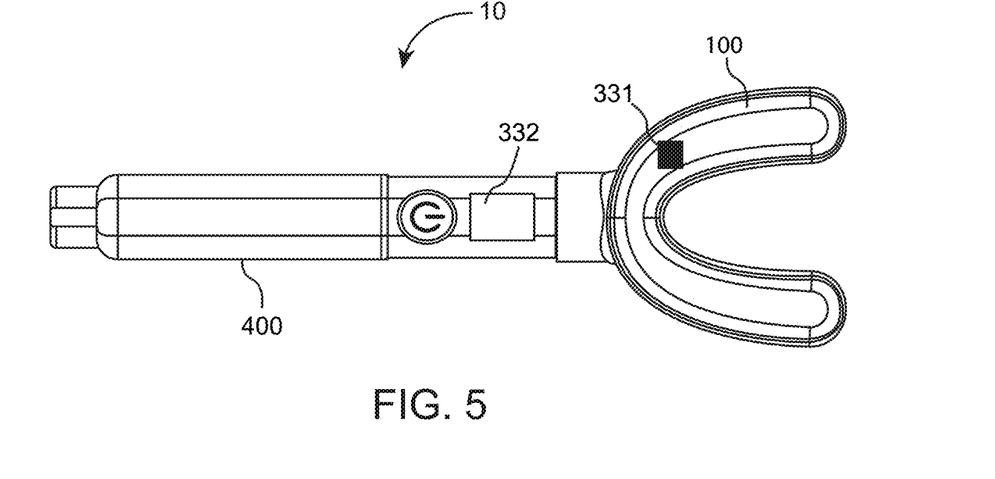
FIG. 5 illustrates the first part 410 and the second part 420 forming an integrated unit in accordance with specific embodiments of the present invention.

FIG. 4 shows a mouthpiece 100 rigidly connected to a handle 400. The handle 400 may include a power button to switch on or off the oral care appliance. The handle 400 can be divided into two tubular parts, a first part 410 and a second part 420. The first part 410 can serve as the proximate component of the device while the second part 420 serves as the distal component of the device. The first part 410 is the removable part of the handle 400 and may include the tag 331. The second part 420 of the handle 400 includes the tag reader 332. In a specific example, the first part 410 of the handle 400 having the tag 331 can be connected or brought in proximity to the second part 420 of the handle 400 having the reader 332 to transmit information between the components. In specific embodiments of the invention, the first part 410 and the second part 420 form an integrated unit comprising the reader 332, and the tag 331 can be embedded within or attached to the mouthpiece 100 (as illustrated in FIG. 5). In the above embodiments, an automatic connection is established simply by bringing the two parts with the tag and the reader within range of each other. No other user activity or user input is required to couple the two devices together. The tag reader 332 can be configured to both write and read data to the tag. Reading data from the tag 331 can be done by means of electromagnetic induction between the loop antenna of the reader 332 and the loop antenna of the tag 331.

In another embodiment of the present invention, the tag 331 can be embedded within or attached to other components of the oral care appliance 10, such as, but not limited to, to the mouthpiece 100, to the supply tank (e.g. the rinse bottle, the dentifrice tube, the dispenser or the like). In some embodiments, the reader 332 can be associated with the oral care appliance 10 in variety of ways. For example, the reader 332 can be provided on the handle 400, on a charging station (not shown), on a detached display module 360, user's smartphone, or on any other means. NFC data communication enables NFC devices to communicate with each other and communicate with multiple passive tags at the same time.

Based on the communication between the tag 331 and the reader 332, the oral care appliance 10 detects the user and obtains information related to the last brushing event performed by the user. For example, day, date, brushing time, brushing pattern used, time elapsed since a last brushing event performed by the user, or the like. Specifically, based on the obtained information, the adapting means 300 may adapt the at least one brushing cycle by modifying one or more operational characteristics defined above. The adapting means 300 is also configured to measure the time taken to complete the adapted brushing cycle based on the time elapsed since a last brushing event. A timer or a clock located on the device can be used to measure the time, or a network accessible clock can be accessed to measure the passage of time.

In specific embodiments, instead of using the NFC module (NFC tag 331 and NFC reader 332) the mouthpiece 100, the handle 400, or the like may include a barcode, quick response (QR) code, electrical contacts, a color code, or other scannable code which may be read by the other components of the oral care appliance 10 or any other external devices. The codes may include the same or similar information that may be included on the NFC module.

In specific embodiments, the adapting means 300 is configured to permit the user to adapt the brushing cycle operated according to one or more operational characteristics defined by the brushing profile of the user. The adapting means 300 can be configured to be responsive to voice commands to adapt the brushing cycle. The components of the adapting means 300 can use a variety of arrangements, singly or in combination to implement data communication between each other. The adapting means 300 can be incorporated in the mouthpiece 100, the handle 400, or a combination of the two.

In specific embodiments, a method of adapting at least one brushing cycle of an oral care appliance is provided. The method comprises identifying a user; determining a time elapsed since a last brushing event performed by the user; and adapting the at least one brushing cycle based on the time elapsed since a last brushing event performed by the user. The oral care appliance comprises an adapting means configured to adapt the at least one brushing cycle. The oral care appliance further comprises a mouthpiece configured to be actuated during the at least one brushing cycle and a means to supply a cleaning agent into the mouthpiece during the at least one brushing cycle.

Figure 6:
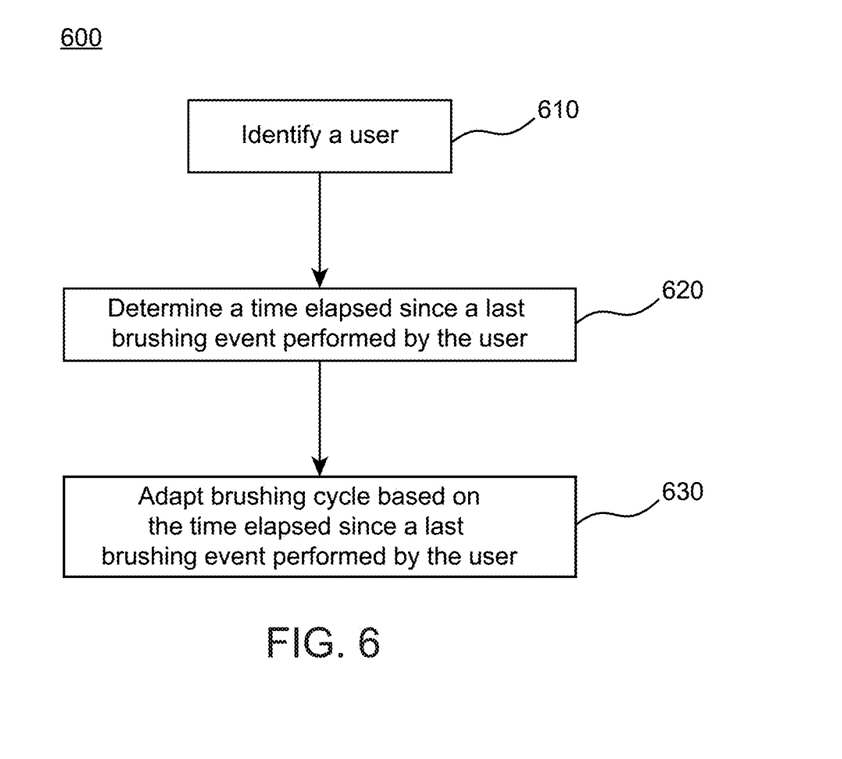
FIG. 6 schematically shows an example flow diagram of a method 600 of adapting at least one brushing cycle of the oral care appliance 10 in accordance with specific embodiments of the present invention.

FIG. 6 schematically shows an example flow diagram of a computerized method 600 to facilitate adaptation of at least one brushing cycle of an oral care appliance 10 as shown in FIGS. 1, 4, and 5, arranged in accordance with specific embodiments described herein.

Method 600 may include one or more operations, actions, or functions as illustrated by one or more of blocks 610, 620, and/or 630. Although illustrated as discrete blocks, various blocks may be divided into additional blocks, combined into fewer blocks, or eliminated, depending on the desired implementation. In some further examples, the various described blocks may be implemented as a parallel process instead of a sequential process, or as a combination thereof. Execution of the steps of method 600 can involve a non-transitory computer-readable medium on an oral care appliance storing executable instructions that cause a control system of the oral care appliance to carry out the illustrated steps. The control system can include the adapting means 300 described above.

Figure 7:
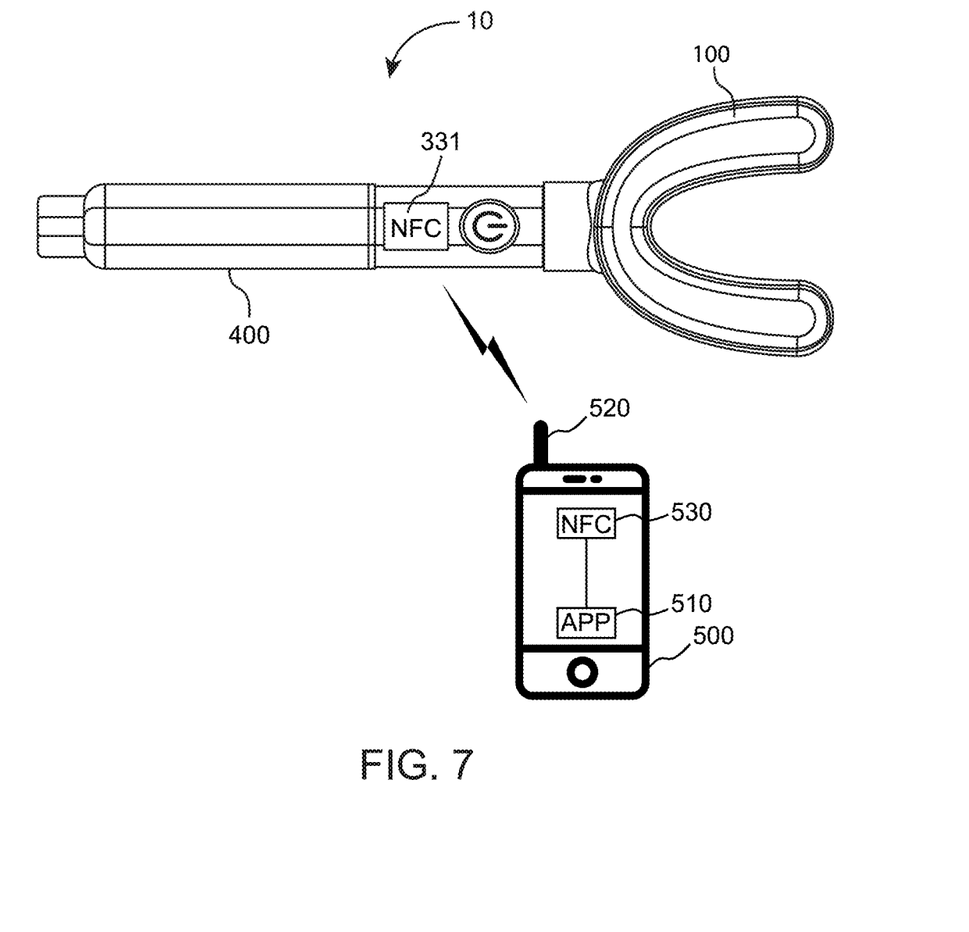
FIG. 7 shows an arrangement of the oral care appliance 10 in communication with external device 500 in accordance with specific embodiments of the present invention.

At block 610, the oral care appliance 10 is configured to determine the identity of a user via the adapting means 300. In some embodiments, the adapting means 300 is configured to store (in memory module 320) an identifier that may be used to identify the user. In some embodiments, the adapting means 300 is configured to communicate via various types of wireless technologies, such as, but not limited to, RFID, Bluetooth, Bluetooth Low Energy, Wifi connections, Zigbee, Z-Wave, and other such technologies. In some embodiments, the adapting means 300 is configured to identify the voice or the image of the user. In some embodiments, the adapting means 300 is configured to communicate with the smartphone of the user to identify the user (as illustrated in FIG. 7). In some embodiments, the adapting means is configured to identify the user by interrogating a tag, QR code, transmitter, memory module, or other source of data located on a proximate component of the oral care appliance. In these approaches, a user is indirectly identified via their association with said proximate component.

At block 620, the oral care appliance 10 is configured to determine a time elapsed since the user performed his last brushing regime/event. The determination is based on the information which was evaluated by the adapting means 300 during the previous brushing regime/event. In other words, every time the user performs a brushing event, the microprocessor 310 is operated to measure, or assist in measuring, the duration of brushing cycle, the times of day (day, date etc.) the user activates and/or uses the oral care appliance 10, the user's brushing or dental habits, how often (e.g., number of injections) the user uses the cleaning agent 220, pressure values of the oral care appliance 10, any other information associated with the user or with the use of the oral care appliance 10, or a combination thereof. In some embodiments, the oral care appliance 10 is adapted to obtain other information such as, but not limited to, the user's physical characteristics, enamel health, sensitivity, medical record, periodontal condition, personalized programs, any calculations performed by the adapting means 300, any information obtained from one or more supply tanks, such as supply tank 210, and any other information. A local timer, local clock, or network accessible clock, can be used to measure the time elapsed since a last brushing event performed by the user.

At block 630, the oral care appliance 10 is configured to adapt the at least one brushing cycle based on the elapsed time since a last brushing event performed by the user. The oral care appliance 10 may modify one or more operational characteristics according to which the at least one brushing cycle is adapted. For example, based on the determined elapsed time (i.e. after how much time the user is brushing), the adapting means 300 may determine that the user has plaque build-up. As another example, based on the obtained information the adapting means 300 may determine that the user did not brush his teeth for the duration recommended by the health care professional. In this case, the adapting means 300 may determine that the user needs to continue using the oral care apparatus 10 for additional brushing cycles until the recommended duration is reached. The adapting means 300 may then proceed to generate and transmit an alert. In some embodiments, an alert is generated from remote servers. The user may be alerted via the display module 360 or by a sound (e.g. speech or other sound), or by the activation of a light (e.g., an LED) on the oral care appliance 10. In some embodiments, based on the determined elapsed time since last brushing, the adapting means 300 is configured to modify the duration of a brushing cycle, brushing frequency, brushing pattern, recommended brushing location, usage of cleaning agent/fluid, or combination thereof.

In specific embodiments of the invention that have been alluded to above, the oral care appliance can be in communication with external devices such as network accessible servers or a user's smartphone. FIG. 7 shows an arrangement of the oral care appliance 10 in communication with external devices, according to another embodiment of the invention. In an example, the oral care appliance 10 communicates wirelessly with the external devices in a bidirectional manner which allows communication of data both to and from the oral care appliance 10. In a specific example, the external device 500 is a smartphone which is operated to communicate with the oral care appliance 10. The external device 500 comprises an antenna 520 which is coupled to communication interface 530. In the specific example, the communication interface 530 is an NFC module. In other examples, the communication interface 530 is any type of wireless technology, such as, but not limited to, RFID, Bluetooth, Bluetooth Low Energy, Wifi connections, Zigbee, Z-Wave, and other such technology. In the specific example of the external device 500 being a smartphone, a smartphone application 510 may present identification data (name, age, sex or occupation etc.) of the user, recommended usage time (e.g., 2 minutes per brushing cycle), usage of cleaning agent/fluid, recommended brushing pressure or location, a personalized program associated with the user, default cycles, and/or analysis of various operational characteristics based on the obtained information. In some embodiments, the external device 500 is configured to track and share information associated with the use of the oral care appliance 10 by a specific user or multiple users. The external device 500 generates and transmits various types of information, notifications and thereby, facilitates the user in improving his or her dental health.

According to a specific embodiment of the invention, the external device 500 is configured to identify the user by bringing the oral care appliance 10 and the external device 500 together such that their antennas are brought within the range of NFC communication. NFC communication uses electromagnetic induction between two loop antennas. By bringing the external device 500 and the oral care appliance 10 together, a smartphone application 510 is automatically initialized and thus appears as the user interface on the external device 500. This enables the external device 500 to act as a computing source controlled by the smartphone application 510 that may be utilized to identify the user that is using the oral care appliance 10. For example, the user may be identified by a name, age, occupation or a demographic information associated with the user. The external device 500 may also monitor other information relating to user's brushing profile, brushing performance, dental habits and dental history, set target goals for a user, and provide a user with requisite adaptation of the brushing cycles, or the like.

In specific embodiments, based on the information about the time elapsed since a last brushing event performed by the user, one or more operational characteristics are modified to adapt the at least one brushing cycle. Examples of such operational characteristics are, but not limited to, number of pulsations (e.g., number of contraction/relaxation phases of the mouthpiece 100), number of injections of the cleaning agent 220, the volume of cleaning agent 220 injected for each injection, total volume of cleaning agent 220 injected, type and composition of the cleaning agent 220, control modes of the pulsations, or a combination thereof. In some embodiments, the brushing cycles may be adapted according to the recommendation by a health care professional or according to the default cycles, especially if it is determined (from tracked information) that the user did not brush his or her teeth for recommended duration. In some embodiments, the brushing cycles may be adapted by modifying one or more operational characteristics described above. In some other embodiments, the adaptation of the brushing cycles is done by utilizing the adapting means 300 of the oral care appliance 10 in combination with at least one of an online source, server, communication network, health care service provider, or external device 500.

In another specific embodiment of the invention, the oral care appliance 10 of FIG. 7 may allow an easy connection to an online source via the external device 500, thereby allowing upload or download of information associated with the user. This enables real-time analysis and dental studies of the user's brushing regime.

Although many of the embodiments provided above were described with reference to oral care appliance 10, the principles and examples may as appropriate be applied to any other appliance for cleaning teeth of a user. In particular, the description may be applicable to any electric toothbrush, a supply tank (i.e. dispenser) for a cleaning agent, or the like.

One or more of the above-mentioned embodiments/steps of the present invention can be automated completely or partially using one or more of components such as an adapting means and software. The means for varying pressure such as valve/pumps can be controlled by use of these components.

It will be appreciated that the above description has described and illustrated specific arrangements of different modules, and processors. However, the description is intended to cover any and all variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed, but that the invention will include all embodiments and arrangements falling within the scope of the appended claims.

What is claimed is:

1. An oral care appliance comprising:
a mouthpiece configured to be actuated during at least one brushing cycle;
a control system configured to actuate the mouthpiece according to the at least one brushing cycle; and
a non-transitory computer-readable medium storing executable instructions to:
determine a time elapsed since a last brushing event; and
adapt the at least one brushing cycle automatically based on the time elapsed since the last brushing event.

2. The oral care appliance according to claim 1, wherein the at least one brushing cycle is operated according to a plurality of operational characteristics.

3. The oral care appliance according to claim 2, wherein at least one of the operational characteristics is defined by at least one of a user, an operator, a health care professional, and at least one default cycle.

4. The oral care appliance according to 3, the non-transitory computer-readable medium storing instructions to:
adapt the at least one brushing cycle by modifying at least one of the operational characteristics.

5. The oral care appliance according to claim 3, wherein:
the operational characteristics is defined by the at least one default cycle; and the at least one default cycle is based on at least one of a time-controlled mode, a volume-controlled mode, a pressure-controlled mode, a frequency-controlled mode, and a user-specific mode.

6. The oral care appliance according to claim 2, wherein the plurality of operational characteristics comprises a defined duration, a defined count, a defined pressure, a defined amount, a defined performance indicator, a type of mouthpiece and a type of cleaning agent.

7. The oral care appliance according to claim 6, wherein:
the at least one brushing cycle comprises at least one contraction phase of the mouthpiece and at least one relaxation phase of the mouthpiece; and
the defined duration is based on at least one of a duration of the at least one brushing cycle, a duration of the contraction phase, a duration of the relaxation phase, a duration between the contraction phase and the relaxation phase, or a combination thereof.

8. The oral care appliance according to claim 7, further comprising:
a flexible membrane of the mouthpiece, configured to deform in response to pressure variations caused in a cavity,
wherein the at least one brushing cycle comprises at least one contraction phase of the mouthpiece and at least one relaxation phase of the mouthpiece;
wherein a volume of the cavity decreases during the contraction phase; and
wherein the volume of the cavity increases during the relaxation phase.

9. The oral care appliance according to claim 6, wherein:
the at least one brushing cycle comprises at least one contraction phase of the mouthpiece and at least one relaxation phase of the mouthpiece; and
the defined count is based on at least one of a count of the contraction phases, a count of the relaxation phases, and a count of injections of a cleaning agent.

10. The oral care appliance according to claim 6, wherein the defined count is based on at least one of a count of contraction phases in the at least one brushing cycle, and a count of relaxation phases in the at least one brushing cycle.

11. The oral care appliance according to claim 6, wherein:
the at least one brushing cycle comprises at least one contraction phase of the mouthpiece and at least one relaxation phase of the mouthpiece; and
the defined pressure is based on at least one of a contraction pressure threshold of the contraction phase, and a relaxation pressure threshold of the relaxation phase.

12. The oral care appliance according to claim 6, wherein the defined amount is based on at least one of an amount of a cleaning agent being supplied into the mouthpiece during the at least one brushing cycle, a composition of the cleaning agent being supplied into the mouthpiece during the at least one brushing cycle, or a combination thereof.

13. The oral care appliance according to claim 1, the non-transitory computer-readable medium storing instructions to:
adapt the at least one brushing cycle according to a personalized program.

14. The oral care appliance according to claim 1, wherein the at least one brushing cycle is adapted using at least one of a communication module, a user interface module, a display module, a timer, a counter, a clock, and a user identification module.

15. The oral care appliance according to claim 1, the non-transitory computer-readable medium storing instructions to:
determine an identity of a user; and
adapt the at least one brushing cycle based on the identity.

16. The oral care appliance according to claim 15, further comprising:
a memory module storing a brushing profile associated with the identity; and
wherein the brushing profile comprises at least one of the times elapsed since a last brushing event performed, a specific information associated with the identity, and a record of previous brushing events.

17. The oral care appliance according to claim 1, further comprising: at least one cavity in the mouthpiece configured to deform and: (i) contract the mouthpiece during a contraction phase of the brushing cycle; and (ii) relax the mouthpiece during a relaxation phase of the brushing cycle.

18. The oral care appliance according to claim 1, further comprising:
at least one supply tank storing a cleaning agent; and
a connection assembly to supply the cleaning agent to the mouthpiece from the supply tank during the at least one brushing cycle.

19. The oral care appliance of claim 1, wherein the non-transitory computer-readable medium is part of the control system and further stores executable instructions to:
receive an identification from the mouthpiece; and
determine the time elapsed since the last brushing event using the identification.

20. A method, in which each step is conducted by a computerized system, of adapting at least one brushing cycle of an oral care appliance having a mouthpiece, the method comprising:
determining a time elapsed since a last brushing event performed by the oral care appliance using a control system of the oral care appliance;
automatically adapting the at least one brushing cycle using the control system of the oral care appliance, based on the time elapsed; and
actuating a mouthpiece of the oral care appliance using the control system according to the at least one brushing cycle.

21. The method according to claim 20, wherein the at least one brushing cycle is operated according to a plurality of operational characteristics.

22. The method according to claim 21, wherein at least one of the operational characteristics is defined by at least one of a user, an operator, a health care professional, and at least one default cycle.

23. The method according to claim 22, wherein: the operational characteristics is defined by the at least one default cycle; and the at least one default cycle is based on at least one of a time-controlled mode, a volume-controlled mode, a pressure-controlled mode, a frequency-controlled mode, and a user-specific mode.

24. The method according to claim 21, wherein the adapting step is conducted by modifying at least one of the operational characteristics.

25. The method according to claim 21, wherein the plurality of operational characteristics comprises a defined duration, a defined count, a defined pressure, a defined amount, a defined performance indicator, a type of mouthpiece and a type of cleaning agent.

26. The method according to claim 20, wherein the adapting step is conducted according to a personalized program.

27. The method according to claim 20, wherein the adapting step is conducted using at least one of a communication module, a user interface module, a display module, a timer, a counter, a clock, and a user identification module.

28. The method according to claim 20, further comprising:
identifying a user; and
adapting the at least one brushing cycle based on the identity of the user.

29. The method according to claim 28, further comprising: storing a brushing profile associated with the user in a memory module, wherein the brushing profile comprises at least one of the times elapsed since the last brushing event and a record of previous brushing events performed by the user.

30. The method according to claim 20, further comprising:
supplying a cleaning agent into the mouthpiece during the at least one brushing cycle.

31. The method according to claim 30, wherein the at least one brushing cycle comprises at least one contraction phase of the mouthpiece and at least one relaxation phase of the mouthpiece.

32. The method of claim 20, further comprising:
receiving, at the control system of the oral care appliance, an identification from the mouthpiece; and
determining, using the control system, the time elapsed since the last brushing event using the identification.

* * * * *